United States Patent
Jiang et al.

(10) Patent No.: US 11,471,476 B2
(45) Date of Patent: Oct. 18, 2022

(54) MICRORNA AND USES THEREOF IN PREVENTION AND/OR TREATMENT OF FIBROPLASIA MEDICAL SIGN AND/OR SYNDROME

(71) Applicant: INSTITUTE OF BASIC MEDICAL SCIENCES, CHINESE ACADEMY OF MEDICAL SCIENCES, Beijing (CN)

(72) Inventors: Chengyu Jiang, Beijing (CN); Jianchao Du, Beijing (CN); Zhu Liang, Beijing (CN); Jiantao Xu, Beijing (CN); Yan Zhao, Beijing (CN)

(73) Assignee: INSTITUTE OF BASIC MEDICAL SCIENCES, CHINESE ACADEMY OF MEDICAL SCIENCES, Beijing (CN)

( * ) Notice: Subject to any disclaimer, the term of this patent is extended or adjusted under 35 U.S.C. 154(b) by 166 days.

(21) Appl. No.: 16/498,435

(22) PCT Filed: Mar. 30, 2017

(86) PCT No.: PCT/CN2017/078815
§ 371 (c)(1),
(2) Date: Sep. 27, 2019

(87) PCT Pub. No.: WO2018/176330
PCT Pub. Date: Oct. 4, 2018

(65) Prior Publication Data
US 2021/0085706 A1    Mar. 25, 2021

(30) Foreign Application Priority Data
Mar. 29, 2017 (CN) .......................... 201710219899.X

(51) Int. Cl.
*C07H 21/04* (2006.01)
*A61K 31/7105* (2006.01)
*C12N 15/10* (2006.01)
*C12N 15/113* (2010.01)
*C12N 15/63* (2006.01)

(52) U.S. Cl.
CPC ........ *A61K 31/7105* (2013.01); *C12N 15/102* (2013.01); *C12N 15/113* (2013.01); *C12N 15/63* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| 2014/0363469 A1 | 12/2014 | Meyers et al. |
| 2015/0121569 A1* | 4/2015 | Combier ................. C07K 5/10 |
| | | 800/285 |
| 2018/0273941 A1 | 9/2018 | Mao et al. |

FOREIGN PATENT DOCUMENTS

| CN | 103627705 | 3/2014 |
| CN | 103800698 | 5/2014 |
| CN | 104147022 | 11/2014 |
| KR | 20120092541 | 8/2012 |
| WO | WO 2005/024061 | 3/2005 |
| WO | WO 2013/109604 | 7/2013 |
| WO | WO 2014/026333 | 2/2014 |
| WO | WO 2015/166060 | 11/2015 |
| WO | WO 2016/065349 | 4/2016 |

OTHER PUBLICATIONS

Kropski et al. ("The genetic basis of idiopathic pulmonary fibrosis." European Respiratory Journal 45.6 (2015): 1717-1727).*
Babalola et al., "The role of microRNAs in skin fibrosis," *Archives of Dermatological Research*, 305(9):763-776, 2013.
Brennan et al., "Lipoxins attenuate renal fibrosis by inducing let-7c and suppressing TGFβR1," *Journal of the American Society of Nephrology*, 24(4):627-637, 2013.
Chen et al., "Expression of antisense of microRNA-26a-5p in mesenchymal stem cells increases their therapeutic effects against cirrhosis," *American Journal of Translational Research*, 9(3):1500-1508, 2017.
Extended European Search Report issued in European Patent Application No. 17903508.4, dated Dec. 8, 2020.
Lyson et al., "MicroRNAs support a turtle + lizard clade," *Biology Letters*, 8(1):104-107, 2011.
Mu et al., "MicroRNA-143-3p inhibits hyperplastic scar formation by targeting connecdtive tissue growth factor CTGF/CCN2 via the Akt/tmTOR pathway," *Molecular and Cellular Biochemistry*, 416(1-2):99-108, 2016.
Van Rooij et al., "Dysregulation of microRNAs after myocardial infarction reveals a role of miR-29 in cardiac fibrosis," *Proceedings of the National Academy of Sciences USA*, 105(35):13027-13032, 2008.
Wang et al., "Mesenchymal Stem Cells Deliver Exogenous MicroRNA-let7c via Exosomes to Attenuate Renal Fibrosis," *Molecular Therapy*, 24(7):1290-1301, 2016.
Yang et al., "Genome-wide analyses of amphioxus microRNAs reveal an immune regulation via miR-92d targeting C3," *The Journal of Immunology*, 190(4):1491-1500, 2013.
Zhang et al., "Identification and developmental profiling of conserved and novel microRNAs in *Manduca sexta,*" *Insects Biochemistry and Molecular Biology*, 42(6):381-395, 2012.
English translation of PCT International Search Report issued in International Application No. PCT/CN2017/078815, dated Jan. 5, 2018.

\* cited by examiner

Primary Examiner — Kimberly Chong
(74) Attorney, Agent, or Firm — ParkerHighlander, PLLC

(57) ABSTRACT

Provided are microRNA from a *rhodiola* root and uses thereof in the prevention and/or the treatment of a fibroplasia medical sign and/or syndrome.

11 Claims, 13 Drawing Sheets

Specification includes a Sequence Listing.

A sequence listing is
MICRORNA AND USES THEREOF IN PREVENTION AND/OR TREATMENT OF FIBROPLASIA MEDICAL SIGN AND/OR SYNDROME

CROSS REFERENCE TO RELATED APPLICATIONS

This application is a national phase application under 35 U.S.C. § 371 of International Application No. PCT/CN2017/078815, filed Mar. 30, 2017, which claims the priority of Chinese Patent Application 201710219899.X, filed with China National Intellectual Property Administration, filed on Mar. 29, 2017, and titled with "MICRORNA AND USES THEREOF IN PREVENTION AND/OR TREATMENT OF FIBROPLASIA MEDICAL SIGN AND/OR SYNDROME". The entirety of each disclosure referenced above is incorporated herein by reference.

Pursuant to 37 C.F.R. 1.821(c), a sequence listing is submitted herewith as an ASCII compliant text file named "UNITP0038US ST25.txt", created on Sep. 26, 2019 and having a size of 5 kilobytes. The content of the aforementioned file is hereby incorporated by reference in its entirety.

FIELD

The present invention relates to a *Rhodiola rosea*-derived small RNA and uses thereof in prevention and/or treatment of fibrotic disease and/or syndrome.

BACKGROUND

Fibrosis is a terminal change of a large class of diseases characterized by fibroblast proliferation and a large number of extracellular matrix aggregation with inflammatory damage and tissue destruction. That is, damaged normal tissue is abnormally repaired, which results in structural abnormalities. Pulmonary fibrosis is a class of diseases that a variety of different reasons, such as toxic substances, autoimmune diseases, side effects of drugs, infections, and severe trauma, cause lung inflammation, and constant alveolar damage, repeat extracellular matrix destruction, repair, rebuild and over-deposition, which result in normal lung tissue changes and loss of function. Currently, there is still no targeted, safe and effective treatment option for fibrosis (including pulmonary fibrosis).

The vast majority of patients with pulmonary fibrosis have no known cause (idiopathic pulmonary fibrosis). This group of diseases is called idiopathic interstitial pneumonia (IIP), which is a large group of interstitial lung diseases. Pulmonary fibrosis seriously affects the human respiratory function, manifested as dry cough, progressive dyspnea (feel short of breath), and the patient's respiratory function continues to deteriorate as the condition and lung damage aggravate. The incidence and mortality of idiopathic pulmonary fibrosis increased year by year, and the average survival after diagnosis is only 2.8 years.

In pulmonary fibrosis patients, the pulmonary alveoli are gradually replaced by fibrous substances, resulting in the hardening and thickening of the lung tissue, the gradual loss of lung gas exchange capacity, as a result, the patients will develop different degrees of hypoxia which lead to dyspnea, and finally die of respiratory failure. Pulmonary fibrosis is one of the four major diseases of respiratory diseases. The etiology is complicated and the pathogenesis is unknown. The available drugs and methods for treating pulmonary fibrosis are very limited, the efficacy is unsatisfactory, and prognosis is very poor. The 5-year survival rate is only 50%.

Currently, the main treatments of pulmonary fibrosis are glucocorticoids, immunosuppressive agents, such as prednisone, cyclophosphamide, and colchicine. Recently, clinical practice has confirmed that the use of glucocorticoids, antibiotics and immunosuppressive agents to combat organ fibrosis can reduce early alveolar inflammation and alleviate clinical symptoms, but it cannot inhibit the development of fibrosis. Long-term high-dose use of hormones and antibiotics not only brings serious complications, but also exacerbates the process of fibrosis. Other treatments, including oxygen use, are only a relief, which cannot fundamentally solve the problem; in addition, lung transplantation in extreme cases is also limited by many application conditions, especially the very limited transplant success rate in patients with end-stage lung disease.

Since the etiology and pathogenesis are unclear, the treatment of fibrosis has always been one of the problems in the medical field. Despite the constant development of new drugs, there is still no satisfactory treatment or preventive drug, or effective treatment option.

Therefore, there is still a great need for effective drugs for treating or preventing fibrosis.

SUMMARY

The inventors have unexpectedly found that some *Rhodiola rosea*-derived sRNAs can effectively and significantly inhibit the expression of fibrosis-related genes in cell models, and/or effectively alleviate mouse lung fibrosis in animal models. The present invention has been completed based on this.

In one aspect, the present disclosure provides a polynucleotide comprising:

A) a sequence set forth in any one of SEQ ID NO: 1, 2, 3, 4, 5, 6, 7, 8, 9, 10, 11, 12, 13, 14, 15, 16 and 17, or a complementary sequence thereof;

B) a sequence having at least 80%, 85%, 90%, 95%, 96%, 97% or 98% identity to the sequence set forth in A), and capable of preventing/treating fibrosis;

C) a sequence hybridizing under a stringent condition to the sequence set forth in A), and capable of preventing/treating fibrosis;

D) a sequence obtained by adding, deleting, or substituting one or more nucleotides in the sequence set forth in A), and capable of preventing/treating fibrosis; or E) a precursor or modified variant of the sequence set forth in A), B), C) or D), and capable of preventing/treating fibrosis.

In another aspect, the present disclosure provides a nucleic acid vector comprising or expressing the polynucleotide of the above first aspect.

In a third aspect, the present disclosure provides a pharmaceutical composition comprising the polynucleotide of the first aspect or the nucleic acid vector of the second aspect of the present disclosure.

In a fourth aspect, the present disclosure provides a method of preventing and/or treating a fibrotic disease and/or syndrome, comprising administering the polynucleotide of the first aspect, the vector of the second aspect, the pharmaceutical composition of the third aspect, and/or an activator capable of activating the endogenous production of the polynucleotide of the present disclosure in vivo to a subject in need thereof. In one embodiment, the method produces the polynucleotide of the first aspect of the present disclosure by endogenous activation in vivo. Accordingly, the present disclosure also provides a polynucleotide, vector, pharmaceutical composition, and activator for the above-mentioned use, and a use thereof in the manufacture of a medicament for preventing and/or treating fibrotic disease and/or syndrome.

Furthermore, correspondingly, in a fifth aspect, the present disclosure also provides an activator capable of activating the endogenous production of the polynucleotid of the present disclosure in vivo.

In a sixth aspect, the present disclosure provides a method of preparing the polynucleotide of the first aspect of the present disclosure, comprising: synthesizing and/or expressing the polynucleotide of the present disclosure by using a nucleic acid vector, and/or endogenously activating a cell having said ability to express the polynucleotides of the present disclosure.

By any of the above-mentioned aspects, the present disclosure can at least achieve the effects of at least one of the following aspects: effectively inhibiting the expression of one or more fibrosis-related genes at the mRNA and/or protein level; and/or effective preventing and/or treating a fibrotic disease and/or syndrome; and/or providing a polynucleotide capable of achieving one or more of the above-mentioned effects.

BRIEF DESCRIPTION OF DRAWINGS

FIG. 1 and FIG. 2 show the results of two experiments respectively. Prevention experiment: MRC-5 cells were transfected with NC sRNA or HJT sRNA for 48 hours and then stimulated with TGF-β1 for 48 hours, and the relevant indicators were detected. Treatment experiment: MRC-5 cells were stimulated with TGF-β1 for 3 hours and then transfected with NC sRNA and HJT sRNA; 72 hours after TGF-β1 stimulation, the relevant indicators were detected.

FIGS. 3 to 6 show the anti-fibrotic effects of HJT-sRNA-m7, HJT-sRNA-a2, HJT-sRNA-h3, and ppe-miR-169c in the MRC-5 fibrosis cell model, sequentially.

Specifically, FIG. 7 shows that HJT-sRNA-a2 effectively reduced bleomycin-induced mortality in mice and slowed down the condition of weight loss of mice at the same time (FIG. 7A); HJT-sRNA-h3 effectively reduced bleomycin-induced mortality in mice and slowed down the condition of weight loss of mice at the same time (FIG. 7B); ppe-miR-169c effectively reduced bleomycin-induced mortality in mice and slowed down the condition of weight loss of mice at the same time (FIG. 7C).

FIG. 8 shows the effect of HJT-sRNA-m7 in the bleomycin-induced mouse pulmonary fibrosis model.

FIG. 9 shows that, in the bleomycin-induced mouse pulmonary fibrosis model, HJT-sRNA-m7 effectively alleviated the symptoms of pulmonary tissue fibrosis, reduced the expression of collagen, fibronectin and α-SMA. Specifically, FIG. 9A shows hydroxyproline content in mouse right lung (µg/right lung); FIG. 9B shows hematoxylin-eosin staining (H&E staining) of mouse lung tissue; FIG. 9C shows the immunohistochemical results of Masson's staining for α-SMA, fibronectin and COL3A1; FIG. 9D shows the pathological statistical results corresponding to FIG. 9C.

FIG. 10 shows luciferase reporter gene assay for verifying the target gene of HJT-sRNA-m7; FIG. 11 shows the luciferase reporter gene assay for verifying the target gene of HJT-sRNA-a2; FIG. 12 shows the luciferase reporter gene assay for verifying the target gene of HJT-sRNA-h3.

DETAILED DESCRIPTION

Figure 1:
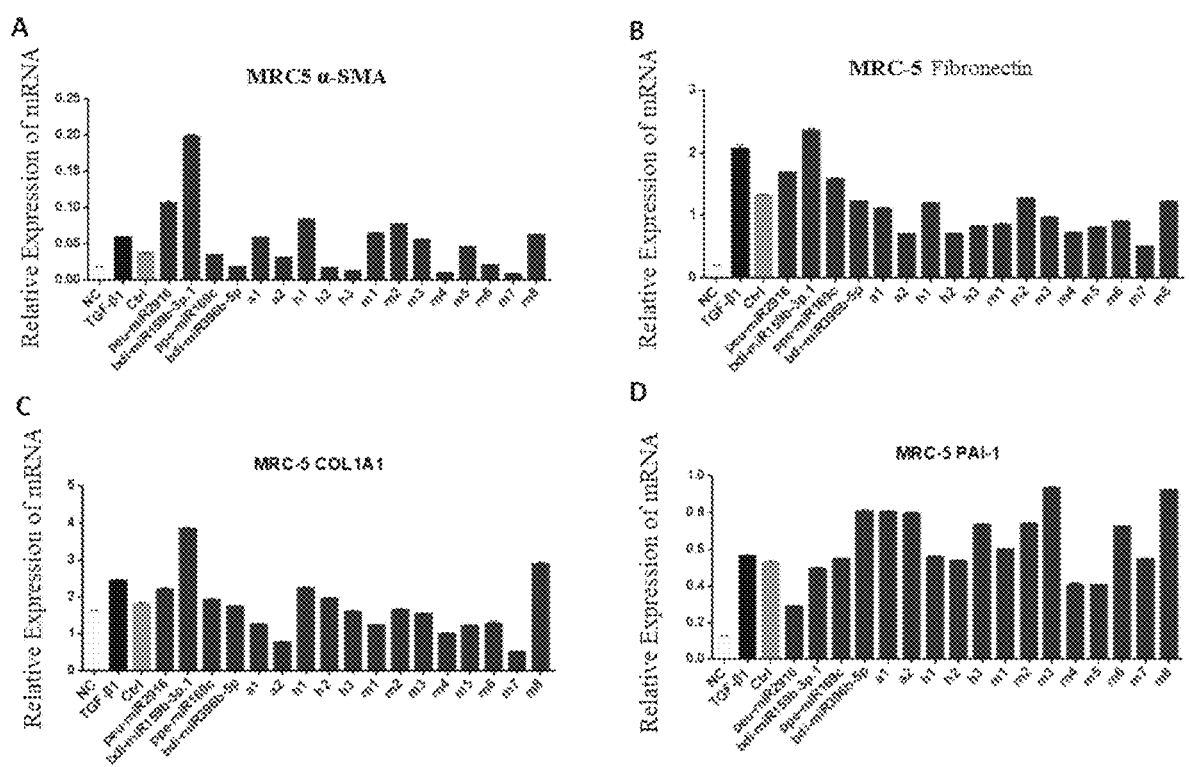
FIG. 1 and FIG. 2 show the screening results of the mRNA expression levels of α-SMA, fibronectin, COL1A1 and PAI-1, that is, four fibrosis-related genes, by using *Rhodiola rosea*-derived sRNA (HJT sRNA) in a TGF-β1-stimulated MRC-5 fibrosis cell model.

The present disclosure is further illustrated in the followings, but it is not intended to limit the invention in any way, and any modifications made based on the teachings of the present disclosure fall within the scope of the present invention.

In general, siRNA, miRNA and other non-coding small RNAs are indiscriminately referred to small RNA (sRNA). Unless otherwise indicated, the term "small RNA (sRNA)" as used herein refers to various non-coding small RNAs including siRNA and miRNA.

As used herein, a small RNA may be non-natural, such as synthetic or expressed from an artificial vector. The term "non-natural" refers to a target substance which is not naturally occurring, and this does not exclude that the non-natural substance has the same structure and/or composition as the naturally occurring substance.

The term "fibrosis" refers to a process and state of increased fibrous connective tissue and decreased parenchymal cells in tissues/organs, which can occur in a variety of tissues/organs, and sustained progression may result in organ structural damage and decline of function, and even failure, which is a serious threat to human health and life.

The term "capable of preventing/treating fibrosis" refers to a target substance which can prevent/treat fibrosis itself or may refer to a substance which can prevent/treat fibrosis and is produced based thereon. That is, this ability does not have to be directly realized by the target substance itself but may be a further application of the consequence produced by the target substance.

The term "inhibit" refers to at least partially reducing or completely eliminating a target activity via a particular treatment.

The terms "include," "comprise," or "contain" means that in addition to the listed features, there may be other additional features. In particular, it is also possible that it may consist of the listed features only.

In one aspect, the present disclosure provides a polynucleotide comprising:

A) a sequence set forth in any one of SEQ ID NO: 1, 2, 3, 4, 5, 6, 7, 8, 9, 10, 11, 12, 13, 14, 15, 16 and 17, or a complementary sequence thereof;

B) a sequence having at least 80%, 85%, 90%, 95%, 96%, 97% or 98% identity to the sequence set forth in A), and capable of preventing/treating fibrosis;

C) a sequence hybridizing to the sequence set forth in A) under a stringent condition, and capable of preventing/treating fibrosis;

D) a sequence obtained by adding, deleting, or substituting one or more nucleotides to the sequence set forth in A), and capable of preventing/treating fibrosis; or E) a precursor or modified variant of the sequence set forth in A), B), C) or D), and capable of preventing/treating fibrosis.

In one embodiment, for the polynucleotide of the present disclosure, wherein the sequence set forth in A) is selected from the group consisting of SEQ ID NO: 3, 10, 13, and 16.

In another embodiment, the polynucleotide is a DNA or RNA, such as a RNA, preferably a small RNA. Specifically, the polynucleotide is 10-50 nucleotides, 12-40 nucleotides in length, such as 16-35 or 18-30 nucleotides; more specifically, the above-mentioned polynucleotide is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

In a specific embodiment, the polynucleotide is single stranded or double stranded, preferably single stranded. In another specific embodiment, the polynucleotide is non-natural, such as synthetic or expressed from an artificial vector.

In a second aspect, the present disclosure provides a nucleic acid vector comprising or expressing the polynucleotide of the above first aspect. For example, specifically, the nucleic acid vector may be a DNA, while the expressed polynucleotide may be a RNA, such as a sRNA.

In a third aspect, the present disclosure provides a pharmaceutical composition comprising the polynucleotide of the first aspect or the nucleic acid vector of the second aspect.

In one embodiment, the pharmaceutical composition further comprises an additional anti-fibrotic agent. Specifically, the additional anti-fibrotic agent may be selected from one or more of the followings: a glucocorticoid such as cortisone acetate, hydrocortisone, prednisolone, dexamethasone, betamethasone, triamcinolone, triamcinolone acetonide, beclomethasone; a immunosuppressive agent such as cyclophosphamide, azathioprine, methotrexate; an antioxidant such as acetylcysteine, carbocisteine; an anticoagulant such as low molecular weight heparin; and colchicine, interferon, ACEI and a statin.

In a fourth aspect, the present disclosure provides a method of preventing and/or treating a fibrotic disease and/or syndrome comprising administering the polynucleotide of the first aspect, the vector of the second aspect, the pharmaceutical composition of the third aspect, and/or an activator capable of activating the endogenous production of the polynucleotide of the present disclosure in vivo to a subject in need thereof. In one embodiment, the method produces the polynucleotide of the first aspect of the present disclosure by endogenous activation in vivo. Accordingly, the present disclosure also provides a polynucleotide, vector, pharmaceutical composition, and endogenous activator for the use in the fourth aspect, and a use thereof in the manufacture of a medicament for prevention and/or treatment of a fibrotic disease and/or syndrome.

In one embodiment, the polynucleotide, vector, pharmaceutical/cosmetic composition of the present disclosure may be formulated for non-invasive administration (e.g., topical administration) and/or administration by injection, for example, it may be formulated for administration via the digestive tract, via the respiratory tract, and/or by injection, such as oral, inhalation, and/or administration by injection.

In some cases, using an invasive route of administration is preferred (such as administration by injection, including intramuscular, subcutaneous, intravenous, intraarterial, intraperitoneal, intra-target injection); while in some other cases, using a non-invasive route of administration is preferred.

In another embodiment, the fibrotic disease and/or syndrome is selected from the group consisting of: fibrotic diseases and/or syndromes of lung, cardiovascular system, liver, pancreas, kidney, spleen, eye, nervous system, bone marrow, and skin.

In a specific embodiment, the fibrotic disease and/or syndrome is selected from the group consisting of:

an occupational inorganic dust disease including silicosis, asbestosis and anthracosis; organic dust and hypersensitivity pneumonitis including farmer's lung, air-conditioner lung, pigeon-breeder's lung and bagassosis; a drug/treatment-related disease, the drug is selected from the group consisting of an antibiotic, a nonsteroidal anti-inflammatory drug, a cardiovascular drug, an antineoplastic agent, an oral hypoglycemic agent, and a morphine; an infectious disease including tuberculosis, viral pneumonia, and pneumocystis infection; a secondary lung disease including a lung disease associated with heart failure, congenital heart disease, adult respiratory distress syndrome, chronic heart failure, and transplant rejection; a primary pulmonary disease including idiopathic interstitial pneumonia, obliterative bronchiolitis with organizing pneumonia, and pulmonary lymphangioleiomyoma; a pulmonary disease associated with a collagen vascular disease including a lung disease associated with systemic lupus erythematosus, rheumatoid arthritis, progressive systemic sclerosis, polymyositis, dermatomyositis, mixed connective tissue disease; an alveolar filling disorder including diffuse alveolar hemorrhage syndrome, alveolar proteinosis, eosinophilic pneumonia, pulmonary vasculitis, lymphocytic interstitial pneumonia, necrotizing sarcoid granulomatosis, familial pulmonary fibrosis;

an ischemic heart disease including alternative and interstitial fibrosis after myocardial infarction; hypertensive heart disease; an inflammatory cardiomyopathy including viral myocarditis; a metabolic cardiomyopathy including hemochromatosis, amyloid cardiomyopathy, glycogen accumulation cardiomyopathy, and diabetic cardiomyopathy; Keshan disease; dilated cardiomyopathy; hypertrophic cardiomyopathy, restrictive cardiomyopathy; arrhythmogenic right ventricular cardiomyopathy;

viral cirrhosis including viral hepatitis B, C and D; schistosomiasis cirrhosis; alcoholic cirrhosis; biliary cirrhosis including primary biliary cirrhosis, secondary gallstones, periportal inflammation; metabolic cirrhosis including hepatolenticular degeneration, hemochromatosis; toxic cirrhosis including organophosphate poisoning, carbon tetrachloride poisoning, hepatotoxic drug poisoning such as isoniazid, tetracycline, chlorpromazine; nutritional cirrhosis; cardiac cirrhosis including chronic congestive heart failure;

acute pancreatitis; pancreatic duct obstruction; chronic alcohol intoxication; sphincter of oddi dysfunction; pancreatic ischemia;

a vascular renal fibrotic disease and/or syndrome including hypertension; an immune renal fibrotic disease and/or syndrome including glomerulonephritis, systemic lupus erythematosus, scleroderma, renal transplant rejection; an infectious renal fibrotic disease and/or syndrome, including pyelonephritis, nephrolithiasis; a metabolic renal fibrotic disease and/or syndrome, including hyperlipidemia, diabetes, hyperuricemia, hypercalciuria;

a spleen fibrotic disease;

an eye fibrotic disease and/or syndrome after eye trauma and surgery, diabetic retinal ocular fibrosis;

a fibrotic disease and/or syndrome after spinal trauma, stroke scar formation, Alzheimer's disease;

idiopathic and drug-induced myelofibrosis, polycythemia vera; chronic myeloid leukemia, and Hodgkin's disease; and a dermal fibrotic disease and/or syndrome including oral mucosal fibrosis, scarring, a bump, and pachydermia.

In another embodiment, the method further includes administering an additional anti-fibrotic agent separately and/or together, temporally and/or spatially, to a subject in need thereof. Specifically, the additional anti-fibrotic agent may be selected from any one or more of the followings: a glucocorticoid such as cortisone acetate, hydrocortisone, prednisolone, dexamethasone, betamethasone, triamcinolone, triamcinolone acetonide, beclomethasone; a immunosuppressive agent such as cyclophosphamide, azathioprine, methotrexate; an antioxidant such as acetylcysteine, carbocisteine; an anticoagulant such as low molecular weight heparin; and colchicine, interferon, ACEI and a statin.

In another embodiment, the method includes producing the polynucleotide of the first aspect of the present disclosure by endogenous activation in vivo. For this purpose, the present disclosure also provides an activator capable of activating the endogenous production of the polynucleotide of the present disclosure in vivo.

In another aspect, the present disclosure provides a cosmetic method of skin rejuvenation including administering the polynucleotide, the vector, the pharmaceutical/cosmetic composition, and/or the activator capable of activating the endogenous production of the polynucleotide of the present disclosure in vivo to a subject in need thereof. In one embodiment, the above-mentioned substance is administered via a non-invasive route, such as topical administration.

In another aspect, the present disclosure provides a method of preparing the polynucleotide of the first aspect, including synthesizing and/or expressing the polynucleotide of the first aspect of the present disclosure from a nucleic acid vector.

EXAMPLES

The following examples with reference to the drawings are merely illustrative of the invention disclosed herein, and are not to be construed as limiting the protection scope of the appended claims.

1. Experiment-related Methods and Processes
1.1 Extraction and Purification of *Rhodiola rosea* RNA Small RNA extraction from fresh *Rhodiola rosea* was performed according to the manufacturer's instructions of the miRNeasy Mini Kit (QIAGEN #217004). RNA Extraction from liquid:

(1) In 200 µl of *Rhodiola rosea* sap, 1 ml of CTAB lysis buffer was added, and 20 µl of β-mercaptoethanol was added thereto, shaken vigorously;

(2) the mixture was subjected to constant oscillation and vortex at 65° C. for 30 minutes;

(3) the mixture was centrifuged at 4° C., 12,000 rpm for 7 minutes, 800 µl of the supernatant was taken, 380 µl of ethanol was added, mixed well;

(4) the mixture was placed at 4° C. for 20 minutes;

(5) the mixture was centrifuged at 4° C., 12,000 rpm for 15 minutes, 800 µl of the supernatant was taken, 0.8 volumes of chloroform was added, mixed vigorously;

(6) the mixture was placed for 10 minutes, centrifuged at 4° C., 12,000 rpm for 15 minutes;

(7) 600 µl of the supernatant was taken, 600 µl of pre-chilled isopropanol was added, mixed well, and the mixture was placed at -20° C. for 20 minutes;

(8) the mixture was centrifuged at 4° C., 12,000 rpm for 10 minutes, the supernatant was discarded, the precipitate was washed twice with 75% ethanol;

(9) RNA was dissolved in DEPC-treated $H_2O$.

1.2 Extraction and High-throughput Sequencing of Total RNA from Human Blood, Mouse Lung and Cells (1) TRIzol lysis buffer was added to the cells, placed at room temperature for 5 minutes (for mouse lung tissue, 1.0 ml of TRIzol lysis buffer was added to 100 mg of tissue, grind with a homogenizer, centrifuged at 4° C., 12,000 rpm for 10 minutes, the tissue precipitate which was not homogenized was discarded);

(2) the mixture was centrifuged at 4° C., 12,000 rpm for 5 minutes, and the precipitate was discarded;

(3) Chloroform was added in a ratio of 200 µl/ml TRIzol to the mixture, thoroughly shaken and mixed well, placed at room temperature for 15 minutes;

(4) the mixture was centrifuged at 4° C., 12,000 rpm for 15 minutes, the upper aqueous phase was aspirated and added to another centrifuge tube;

(5) Step 4 was repeated, according to the upper aqueous phase, an equal amount of chloroform was added, thoroughly mixed, placed at room temperature for 10 minutes, centrifuged at 4° C., 12,000 rpm for 15 minutes;

(6) the upper aqueous phase was aspirated and added into another new EP tube, 0.5 ml of isopropanol per 1 ml of TRIzol was added, mixed well, placed at room temperature for 5 to 10 minutes;

(7) the mixture was centrifuged at 4° C., 12,000 rpm for 10 minutes, the supernatant was discarded;

(8) 1 ml of 75% ethanol was added, shaken gently, the precipitate was suspended;

(9) the mixture was centrifuged at 4° C., 8000 g for 4 minutes, the supernatant was discarded as much as possible;

(10) the precipitate was dried at room temperature for 5 to 10 minutes, RNA was dissolved with 50 µl of DEPC-treated $H_2O$.

1.3 RT-qPCR Detection.

1) Reverse transcription of sRNA to cDNA: Reverse transcription of sRNA to cDNA was performed by the stem-loop method by High-Capacity cDNA Reverse Transcription Kits (Applied Biosystems, Cat. No. 4368813). The reverse transcription system was as follows: 10 µl of template RNA (150 ng/µl), 2.0 µl of 10×RT Buffer, 0.8 µl of 25×dNTP Mix (100 mM), 2.0 µl of U6 RT Primer (10 µM), 2.0 µl of HJT-sRNA-m7 RT Primer (10 µM), 1.0 µl of MultiScribe™ reverse transcriptase, 1.0 µl of RNase inhibitor, 1.2 µl of Nuclease-free $H_2O$. After short-spin centrifugation, the reaction was carried out in a PCR instrument, the reaction conditions were: (1) 25° C., 10 min; (2) 37° C., 120 min; (3) 85° C., 5 min; (4) 4° C., the reaction was terminated. After the completion of the reaction, 20 µl of RNase Free $dH_2O$ was added to a final volume of 40 µl. The used primer sequences were as follows:

```
Human U6 RT:                            (SEQ ID NO: 18)
GTCGTATCCAGTGCAGGGTCCGAGGTATTCGCACTGGAT

ACGACAAAAATATG;
```

```
                                                         (SEQ ID NO: 19)
HJT-sRNA-m7 RT:
GTCGTATCCAGTGCACGCTCCGAGGTATTCGCACTGGAT

ACGACGCTTACAA.
```

2) Quantitative PCR amplification reaction: the total volume of the qPCR reaction system was 10 μl, including: 5 μl of 2× SYBR Green Master Mix, 0.5 μl of forward primer (10 μM), 0.5 μl of reverse primer (10 μM), 1 μl of cDNA obtained by reverse transcription, 3 μl of RNase Free dH$_2$O. LightCycler 480 real-time PCR instrument was used, the PCR reaction conditions were: 95° C., pre-denaturation for 5 minutes, then the PCR amplification cycle: (1) 95° C., 10 s; (2) 55° C., 10 s; (3) 72° C., 20 s; a total of 40 cycles; finally at 40° C. for 10 seconds to cool down. Both the forward and reverse primers of the amplification reaction were designed and synthesized by Beijing Tsingke Biological Technology Co., Ltd. The used primer sequences were as follows:

```
                                                         (SEQ ID NO: 20)
Human U6 F: GCGCGTCGTGAAGCGTTC;

(SEQ ID NO: 21)
Human U6 R: GTGCAGGGTCCGAGGT;

(SEQ ID NO: 22)
HJT-sRNA-m7 F: TCGCGCTGAGGTAGTAGGTT;

(SEQ ID NO: 23)
HJT-sRNA-m7 R: GTGCACGCTCCGAGGT.
```

3) The relative expression level was calculated by the 2-ΔCt method.

1.4 Protein Sample Collection and Determination of Concentration by BCA Assay (1) The culture medium was discarded, the cells were washed twice with PBS buffer, and an appropriate amount of pre-chilled RIPA lysis buffer was added; the cells were scraped with a pipette tip and transferred into a centrifuge tube, put on ice for 20 minutes; (2) BCA reagents A and B (50:1, v/v) were thoroughly mixed to prepare a BCA working solution;

(3) 25 μl of freshly prepared BSA standard solution and sample to be tested were taken, respectively, and added into a 96-well plate; 200 μl of BCA working solution was added into each well, mixed well;

(4) the plate was incubated at 37° C. for 30 minutes, then cooled to room temperature or placed at room temperature for 2 hours;

(5) the absorbance was measured at 562 nm using an ultraviolet spectrophotometer (Synergy 4 multi-mode microplate reader), and the protein concentration in the sample was calculated according to the standard curve;

(6) the concentration of the sample was adjusted with RIPA lysis buffer so that the concentration of each sample was the same.

1.5 Western blot Detection (1) Gel preparation: 10% separation gel (lower gel) and 5% stacking gel (upper gel) with 15 lanes were used, equal amount of protein sample was loaded in each lane;

(2) Sample treatment: samples were added to an equal volume of 2× loading buffer, put into heat block at 97° C. for 10 minutes and then placed on ice before use;

(3) Protein electrophoresis: electrophoresis buffer was added, the initial voltage of electrophoresis was 80V; when the bromophenol blue dye reached the separation gel, the voltage was increased to 120 V, and the electrophoresis was continued until the bromophenol blue dye reached the bottom of the separation gel or all of it was out of the gel;

(4) Wet transfer: the system was assembled according to the sequence: (negative pole) sponge-filter paper-gel-PVDF membrane-filter paper-sponge (positive pole); the whole transfer system was placed in a 4° C. cold room; the transfer was performed at 300 mA constant current for 120 minutes;

(5) Blocking: the membrane was placed in 3% BSA blocking buffer and blocked for 1 hour at room temperature;

(6) Primary antibody incubation: after blocking, the PVDF membrane was transferred to a plastic bag, 3% BSA blocking solution containing primary antibody was added (the concentration of the primary antibody was determined according to the instruction of the antibody), the bubbles in the bag were removed; the membrane was incubated at 4° C. overnight in the sealed bag;

(7) Membrane washing: the PVDF membrane was taken out, washed with TBST three times for 10 minutes each;

(8) Secondary antibody incubation: TBST was discarded, 3% BSA blocking solution containing secondary antibody was added, incubated at room temperature for 2 hours;

(9) Membrane Washing: the PVDF membrane was taken out, washed with TB ST three times for 10 minutes each;

(10) Development: color development solution was prepared, the prepared color development solution was added dropwise evenly on the membrane surface bound with protein; the membrane was wrapped carefully with plastic wrap and placed in an X ray film cassette for 10-20 minutes; the film was observed after the reaction of developer and fixer;

(11) Scanning and analysis: the negative film was analyzed and processed by Quantity One software, and the gray value was analyzed using Image J software.

1.6 Establishment of Bleomycin-Induced Pulmonary Fibrosis Mice Model

C57BL/6 male mice aged 6-8 weeks and weighed 20-25 g were used. Bleomycin solution (3.5 U/kg) prepared in 100 μl of saline was infused via bronchi under anesthesia, and 100 μl of saline was administered to the control group. Body weight and mortality of mice were recorded every day. The mice were sacrificed on the 21$^{st}$ day. Right lung was taken for the determination of hydroxyproline, and left lung was fixed in 4% paraformaldehyde, embedded in paraffin, sectioned for hematoxylin-eosin staining (H&E staining), Masson's trichrome staining and immunohistochemistry. The results of histopathological section and fibrosis index were combined to evaluate whether the bleomycin-induced pulmonary fibrosis mice model was successfully established.

1.7 Luciferase Reporter Gene Assay of Target Gene

Experimental Materials

Human embryonic kidney cell 293T; DMEM medium (Dulbecco's Modified Eagle's Medium) with 10% (v/v) fetal bovine serum (FBS); penicillin (100 U/ml) and streptomycin (100 mg/ml); transfection reagents: RNAiMax (Invitrogen) and Lipofectamine 2000 (Invitrogen); dual-luciferase reporter system: psiCHECK2 (Promega C2081).

Experimental Method (1) 293T cells cultured in DMEM medium containing 10% FBS were seeded into a 48-well plate at approximately 3×10$^4$ cells per well, and 100 nM of NC sRNA or sRNA was transfected by RNAiMax (Invitrogen) after cells attached to the bottom;

(2) after 24 hours, psiCHECK2-3'-UTR or psiCHECK2-3'-mUTR plasmid was transfected with Lipofectamine 2000 (Invitrogen);

(3) 8 hours, 14 hours or 24 hours after transfection of the plasmid, the fluorescence intensity was detected according to the method in the manual of Dual-luciferase Assay System (Promega E1910).

2. Test Example 2.1 Identification of *Rhodiola rosea*-Derived sRNA

Referring to item 1.1 above, RNA was extracted from fresh *Rhodiola rosea* and *Rhodiola rosea* after decoction respectively via a kit and a modified CTAB lysis method. Agarose gel electrophoresis showed that the RNA fragment was a~20 nt small RNA fragment (small RNA, sRNA). In the following experiments, whole blood collected at 0 hour and 24 hours from people who have continuously drank *Rhodiola rosea* herbal decoction for 7 days, mouse lung tissue at 12 hours, 24 hours and 48 hours after administration of *Rhodiola rosea*-derived RNA for 3 consecutive days, and A549 cells at 24 hours after the addition of *Rhodiola rosea*-derived RNA were subjected to high-throughput sequencing (SE36, Illumina HiSeq 2500). Small RNA fragments in mouse lung, human blood or A549 cells were analyzed by bioinformatics methods according to the following conditions: (1) *Rhodiola rosea*-derived small RNA presented in human blood, mouse lung tissue or A549 cells; (2) *Rhodiola rosea*-derived small RNA that could not be aligned with human or mouse genomes. By the above-mentioned method, the inventors unexpectedly found 3 *Rhodiola rosea*-derived small RNAs entered human blood (see Table 1), and they were sequentially named HJT-sRNA-h1-3 according to their relative abundance in human blood; 8 *Rhodiola rosea*-derived small RNAs entered mouse lung tissue (see Table 2), and they were sequentially named HJT-sRNA-m1-8 according to their relative abundance in mouse lung tissue; 2 *Rhodiola rosea*-derived small RNAs entered A549 cells, and they were sequentially named HJT-sRNA-a1-2 according to their relative abundance in A549 cells (see Table 3). In addition, the inventors also screened out 4 small RNAs in *Rhodiola rosea* that could be aligned with the miRbase database for subsequent experiments (see Table 4).

TABLE 1

Sequence and Naming of *Rhodiola Rosea*-derived sRNA presented in Human Blood

| SEQ ID NO | Name | Sequence | Length |
|---|---|---|---|
| 1 | HJT-sRNA-h1 | AUCCCCACUGCUAAAUUUGACU | 22 |
| 2 | HJT-sRNA-h2 | GCUGGCCCGAUGGUAGUGGGUUAUC | 25 |
| 3 | HJT-sRNA-h3 | UGGGGCUACGCCUGUCUGAGCGUCGCU | 27 |

TABLE 2

Sequence and Naming of *Rhodiola Rosea*-derived sRNA presented in Mouse Lung Tissue

| SEQ ID NO | Name | Sequence | Length |
|---|---|---|---|
| 4 | HJT-sRNA-m1 | UGUCUCGUACCGUGAGUAAUAAUGCG | 26 |
| 5 | HJT-sRNA-m2 | GCUGAGAUGAAGCACUGUAGCUC | 23 |
| 6 | HJT-sRNA-m3 | GUUAUUCAAGUAAUCCAGGAUAGGCU | 26 |
| 7 | HJT-sRNA-m4 | UCUGAGGUAGUAGGUUGUAUGGUUAU | 26 |
| 8 | HJT-sRNA-m5 | GUAUGUAAACAUCCUCGACUGGAAGCU | 27 |
| 9 | HJT-sRNA-m6 | GUUAUGAGGUAGUAGAUUGUAUAGU | 25 |
| 10 | HJT-sRNA-m7 | UGAGGUAGUAGGUUGUGUGGUUGUAAGC | 28 |
| 11 | HJT-sRNA-m8 | GACGGUCGUACCGUGAGUAAUAAUGCGA | 28 |

TABLE 3

Sequence and Naming of *Rhodiola Rosea*-derived sRNA presented in A549 Cells

| SEQ ID NO | Name | Sequence | Length |
|---|---|---|---|
| 12 | HJT-sRNA-a1 | UAGCACCAUUGAAAUCAGU | 19 |
| 13 | HJT-sRNA-a2 | UAGCACCAUCCGAAAUCGGUA | 21 |

TABLE 4

Sequence and Naming of *Rhodiola Rosea*-derived sRNA aligned with the miRbase Database

| SEQ ID NO | Name | Sequence | Length |
|---|---|---|---|
| 14 | peu-miR2916 | UGGGGACUCGAAGACGAUCAUAU | 23 |
| 15 | bdi-miR159b-3p.1 | UUUGGAUUGAAGGGAGCUCUG | 21 |
| 16 | ppe-miR169c | CAGCCAAGGAUGACUUGCCGG | 21 |
| 17 | bdi-miR396b-5p | UCCACAGGCUUUCUUGAACUG | 21 |

Figure 2:
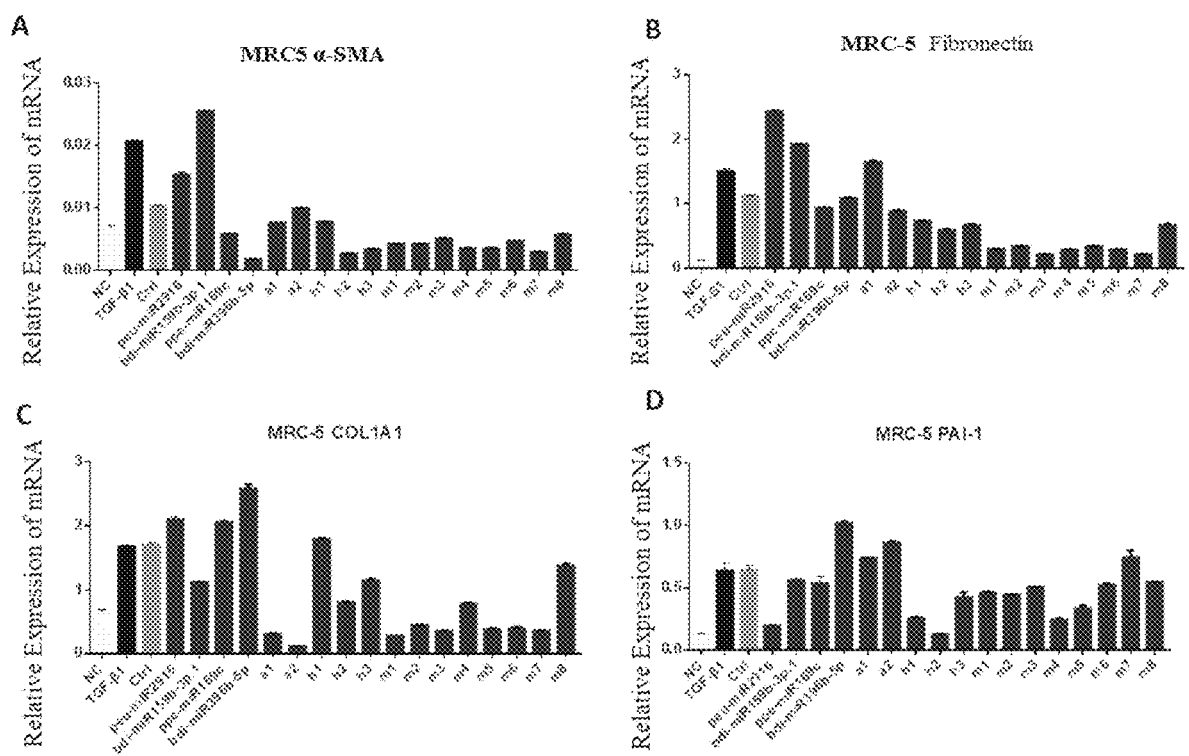
Figure 3:
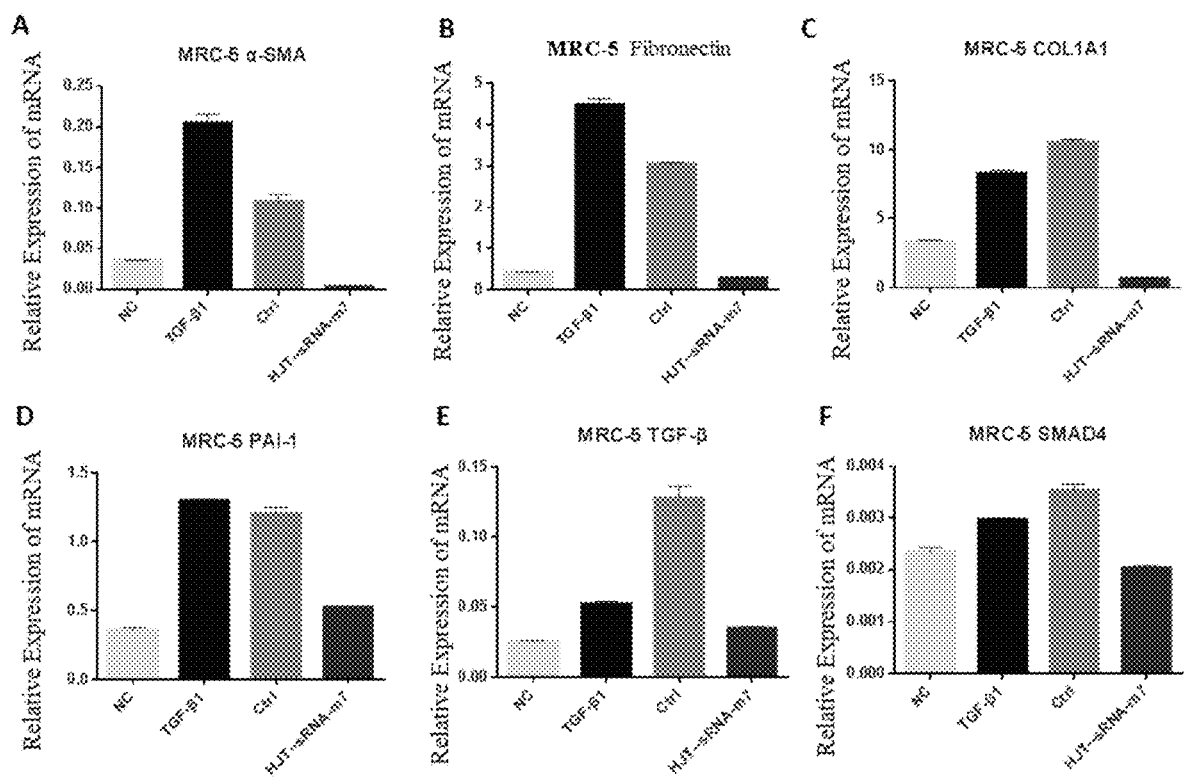
FIGS. 3 to 6 show that, in the TGF-β1-stimulated MRC-5 fibrosis cell model, the selected four *Rhodiola rosea*-derived sRNAs could effectively reduce the mRNA expression levels of α-SMA, fibronectin, COL1A1, PAI-1, TGF-β and SMAD4. Specifically.
Figure 4:
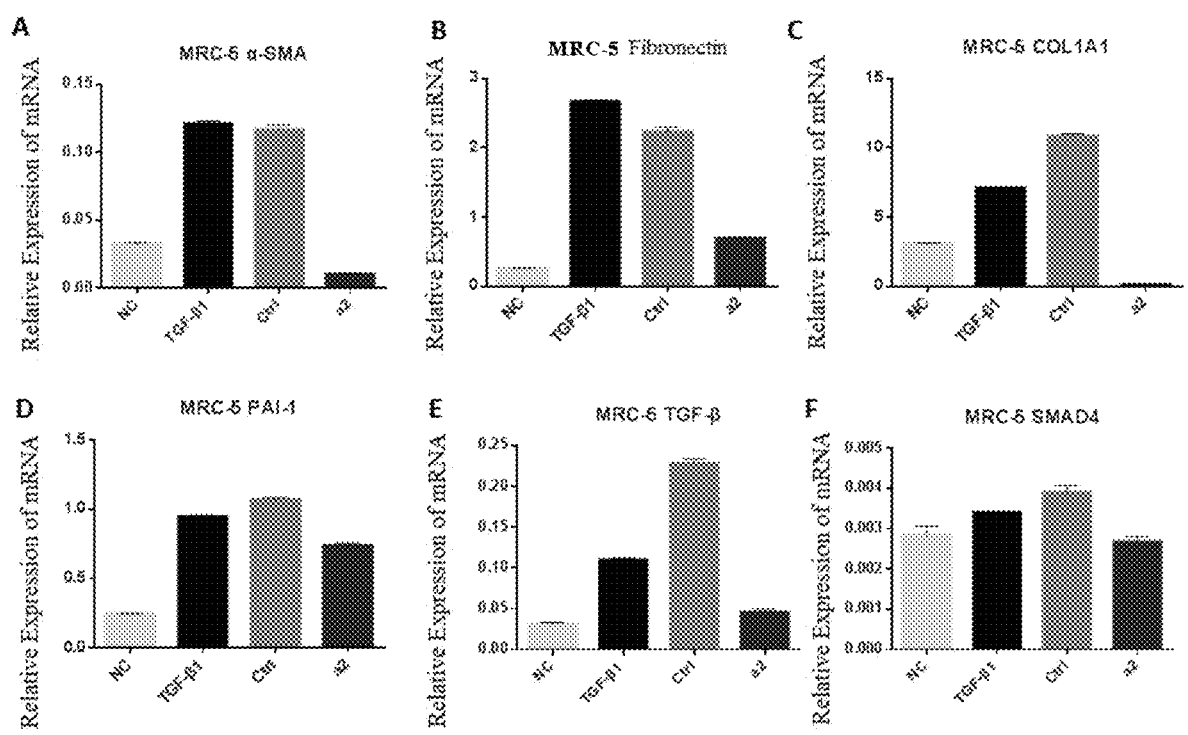
Figure 5:
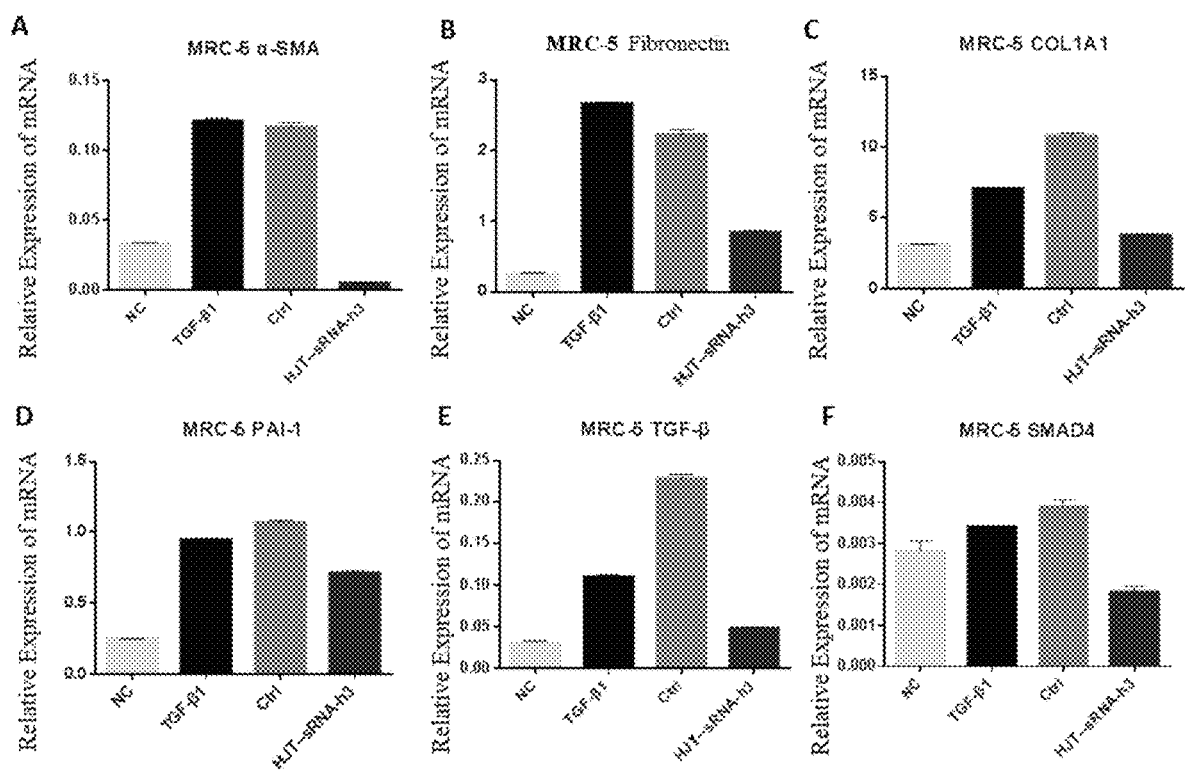
Figure 6:
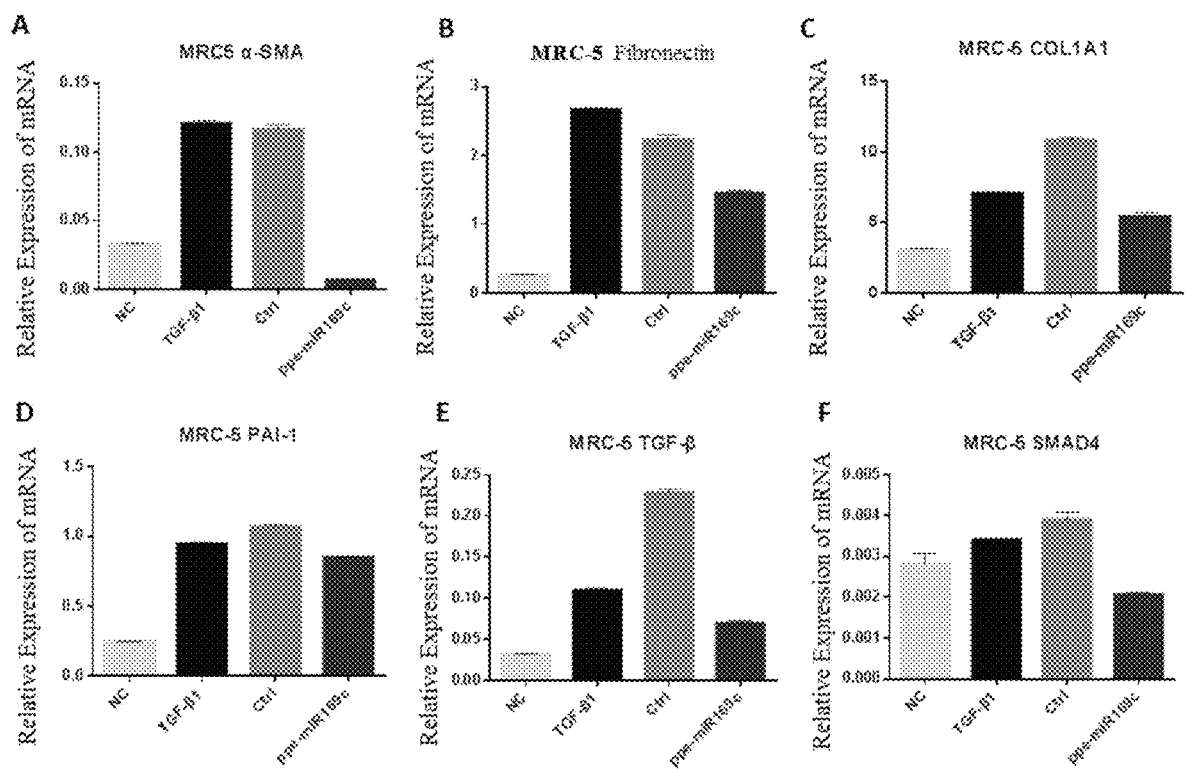

2.2 Anti-fibrotic Activity of sRNA 2.2.1 Screening and Verification of *Rhodiola Rosea*-Derived sRNA in TGF-β1-stimulated MRC-5 Fibrosis Cell Model MRC-5 cells were stimulated with 3 ng/ml TGF-β1 for 48 hours (FIG. 1) or 72 hours (FIGS. 2 to 6), RNA samples were collected. The mRNA relative expression levels of fibrosis-related genes α-SMA, Fibronectin, COL1A1, PAI-1, SMAD4 and TGF-β were detected by RT-PCR.

α-SMA, fibronectin, COL1A1 and PAI-1 are four fibrosis-related genes. The TGF-β1-stimulated MRC-5 fibrosis cells were treated with *Rhodiola rosea*-derived sRNA and the mRNA expression levels of the above-mentioned four fibrosis-related genes were detected, thereby to screen for anti-fibrotic function on small RNAs presented in human blood, lung of mouse and A549 cells. The results are shown in FIGS. 1 and 2, in both prevention group and treatment group, a variety of *Rhodiola rosea*-derived sRNA could inhibit the expression of fibrosis-related genes at mRNA level in MRC-5 cells.

Four sRNA sequences HJT-sRNA-m7, HJT-sRNA-h3, HJT-sRNA-a2 and ppe-miR169c were selected for subsequent verification experiments. NC sRNA and HJT sRNA were transfected into the cells 24 hours in advance, MRC-5 cells were stimulated by TGF-β1 for 72 hours, and relevant indicators were detected. As shown in FIG. 3-6, respectively, in the TGF-β1-stimulated MRC-5 fibrosis cell model, the above-mentioned four sRNAs could effectively reduce the mRNA expression levels of α-SMA, fibronectin, COL1A1, PAI-1, TGF-β and SMAD4.

Figure 13:
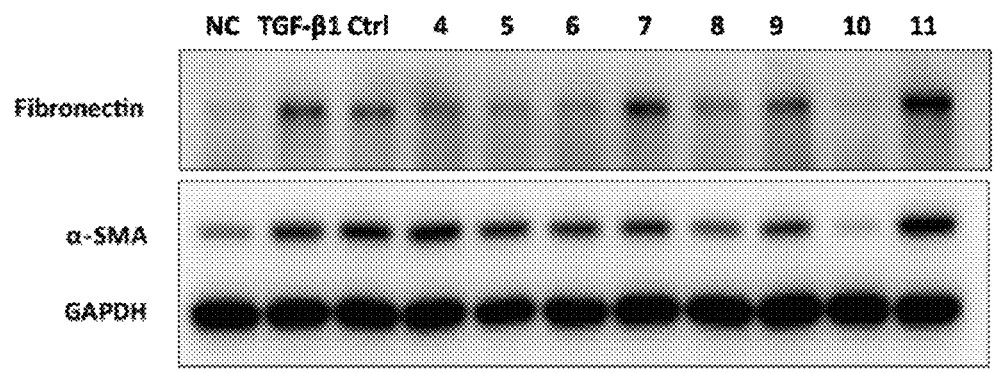
FIGS. 13 to 14 show the screening results of protein expression levels of two fibrosis-related genes α-SMA and fibronectin by using *Rhodiola rosea*-derived sRNA (HJT sRNA) in the TGF-β1-stimulated MRC-5 fibrosis cell model.
Figure 14:
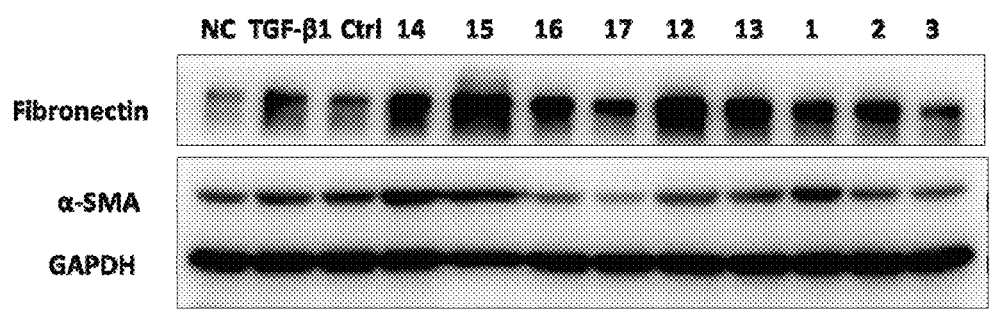

The inventors screened the *Rhodiola Rosea*-derived sRNA (HJT sRNA) at protein expression level of two fibrosis-related genes, α-SMA and fibronectin, in TGF-β1-stimulated MRC-5 fibrosis cell model. FIG. 13 and FIG. 14 show the results of experiment (the prevention group) in which NC sRNA and HJT sRNA were transfected 24 hours in advance, and then MRC-5 cells were stimulated by TGF-β1 for 72 hours, and relevant indicators were detected. As shown in FIG. 13 and FIG. 14, a variety of *Rhodiola rosea*-derived sRNA could inhibit the expression of fibrosis-related genes at protein level in MRC-5 cells. Wherein, the HJT sRNA corresponding to SEQ ID NO: 4, 5, 6, 8, and 10 could significantly reduce the protein expression level of fibronectin, and the HJT sRNA corresponding to SEQ ID NOs: 3, 5, 6, 8, 10, 16, 17 could reduce the protein expression level of α-SMA.

Figure 7:
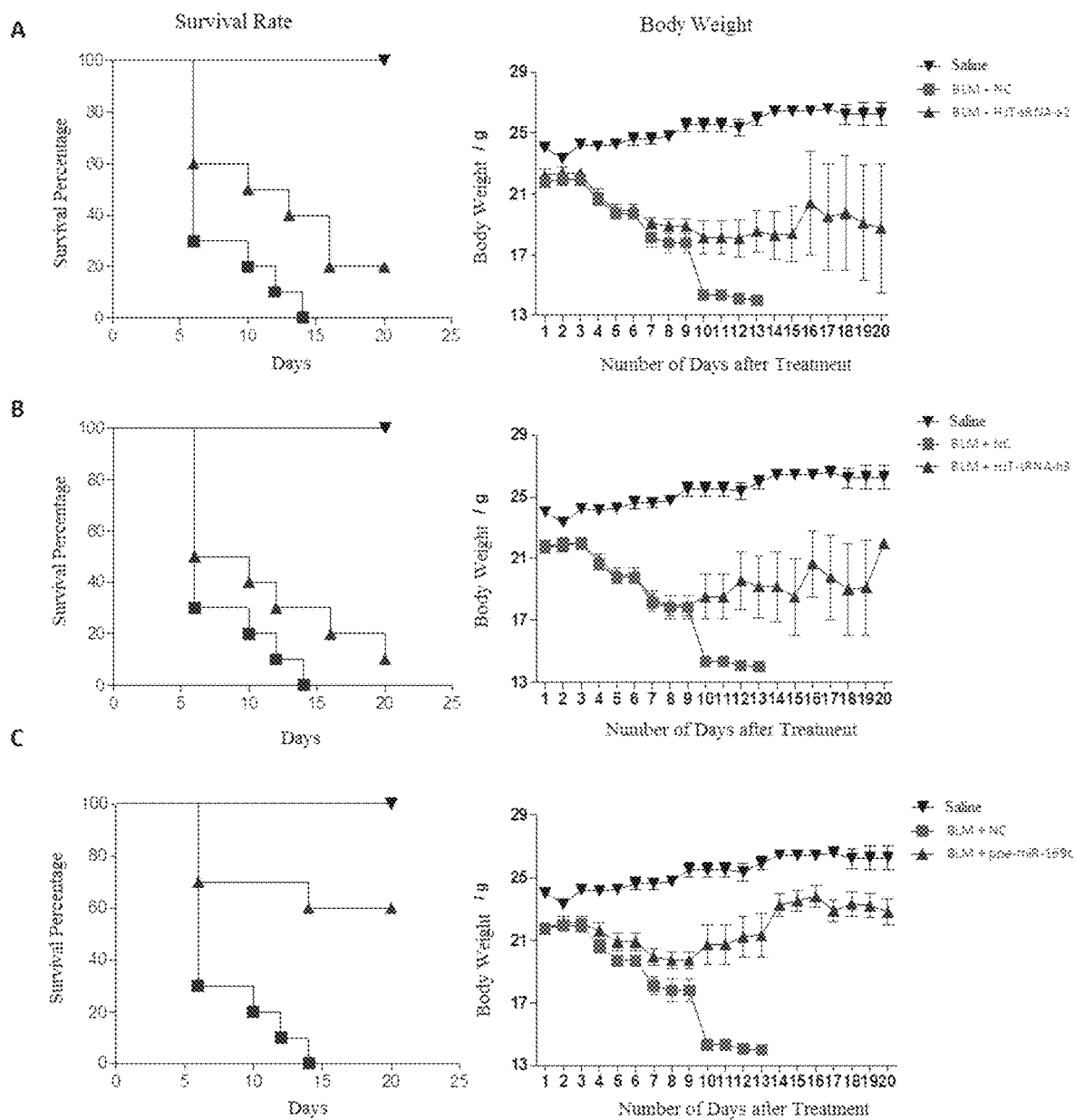
FIGS. 7 to 9 show the results that, in the bleomycin-induced mouse pulmonary fibrosis model, all of the selected four *Rhodiola rosea*-derived sRNAs could effectively reduce the mortality in mice, significantly slow down the trend of weight loss in mice, and alleviate the symptoms of pulmonary fibrosis in mice.
Figure 8:
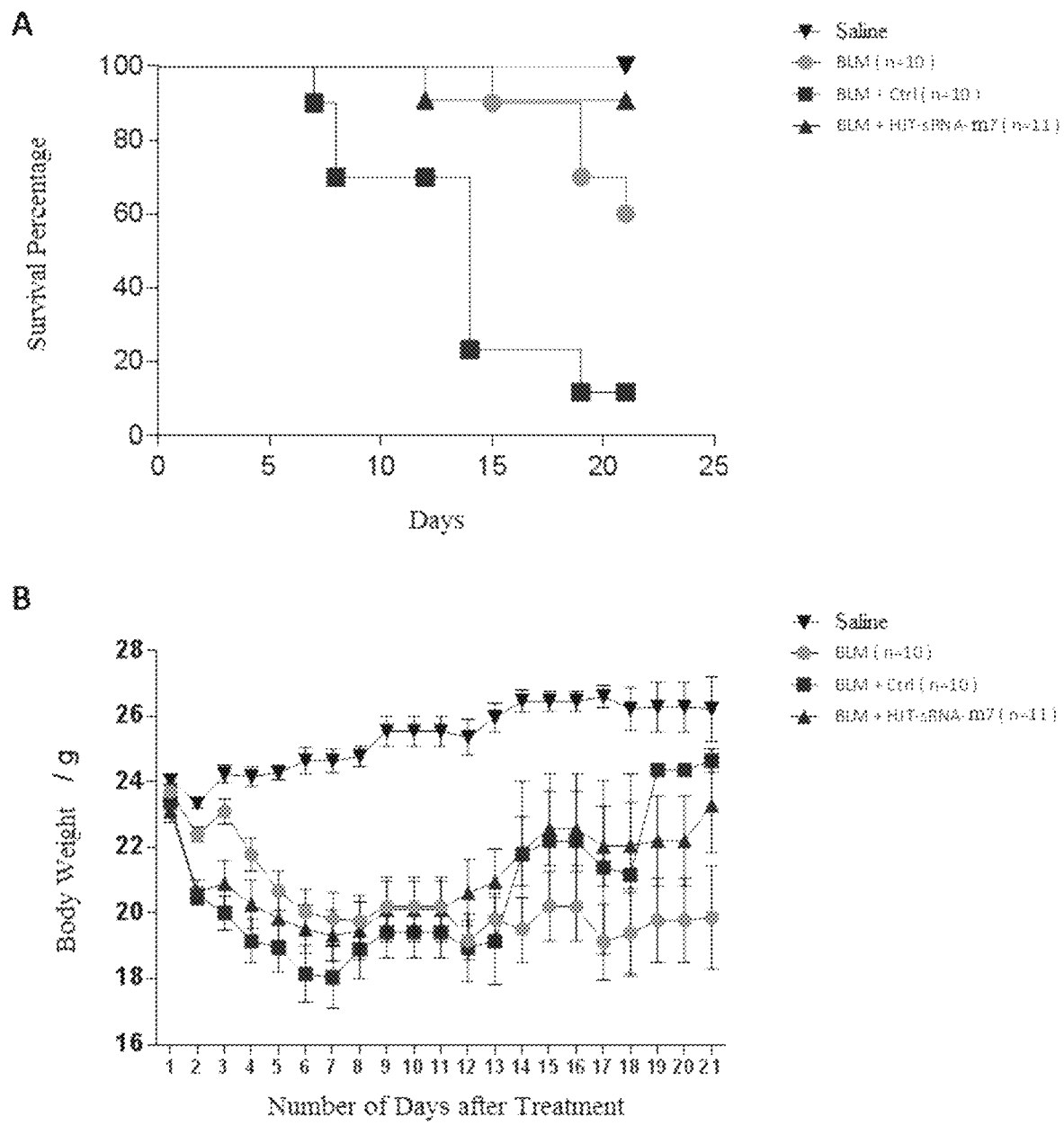
Figure 9:
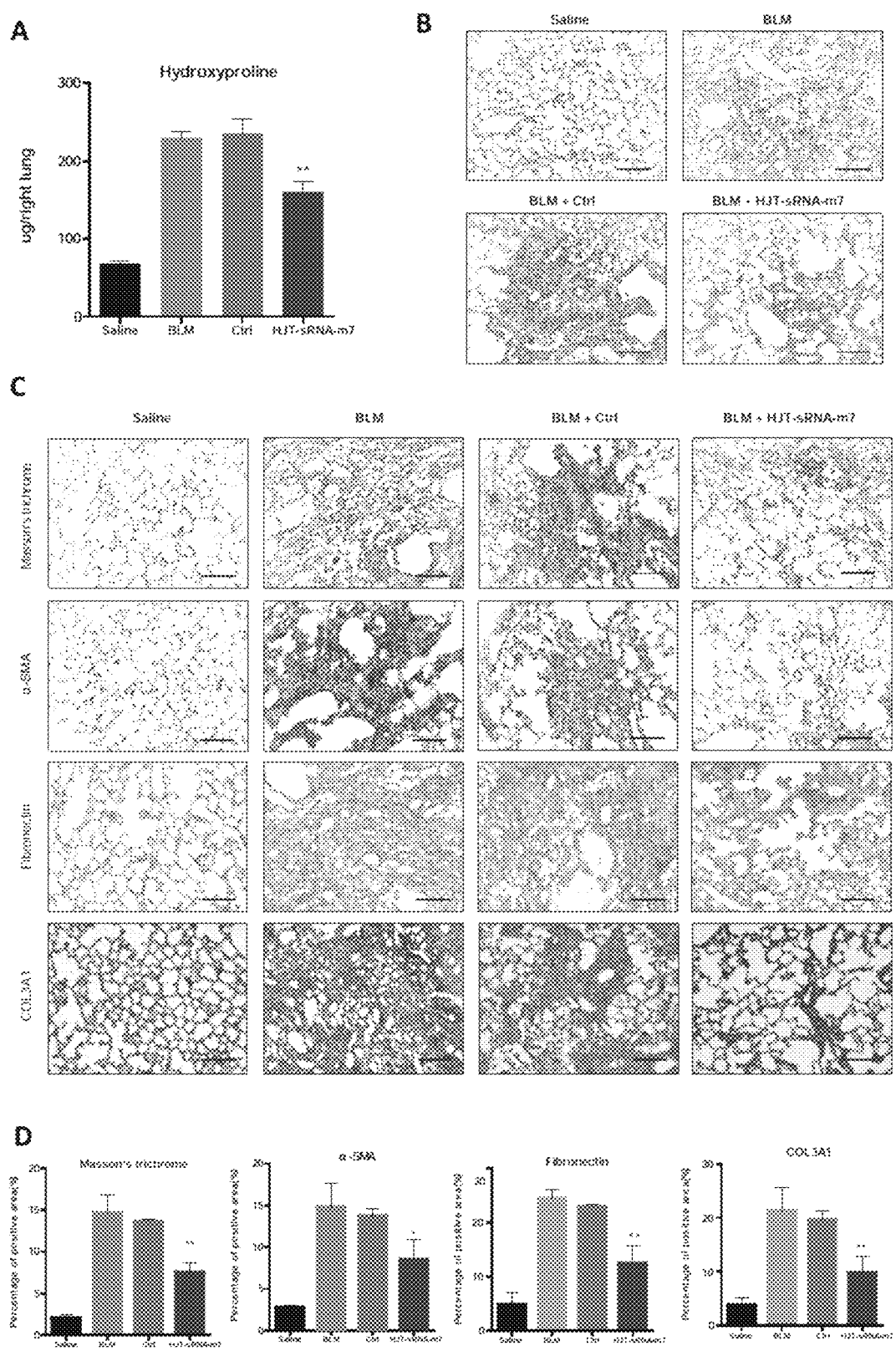

2.2.2 The Effect of *Rhodiola Rosea*-derived sRNA on Bleomycin-Induced Pulmonary Fibrosis Mice Model Referring to item 1.6 above, the effect of the above-mentioned four *Rhodiola rosea*-derived sRNAs on fibrosis were tested in bleomycin-induced pulmonary fibrosis model in mice. C57BL/6J mice were intratracheally injected with bleomycin (BLM, Nippon Kayaku, Tokyo, Japan) at a dose of 3.5 U/kg, while agomir (customized by Suzhou GenePharma Co., Ltd) of NC sRNA, HJT-sRNA-m7, HJT-sRNA-a2, HJT-sRNA -h3 and ppe-miR-169c were intratracheally administered at a dose of 8 mg/kg, diluted with saline to a total volume of 100 μl. Agomir of NC sRNA, HJT-sRNA-m7, HJT-sRNA-a2, HJT-sRNA -h3 and ppe-miR-169c were abdominally injected on the $7^{th}$ day, $13^{th}$ day and $16^{th}$ day after bleomycin was administered, and the dose was 4 mg/kg. As shown in FIGS. 7-9, it was found that the selected four *Rhodiola rosea*-derived sRNAs could surprisingly and significantly reduce the mortality of mice, significantly slowed down the trend of weight loss in mice, alleviate the symptoms of pulmonary fibrosis in mice.

Figure 10:
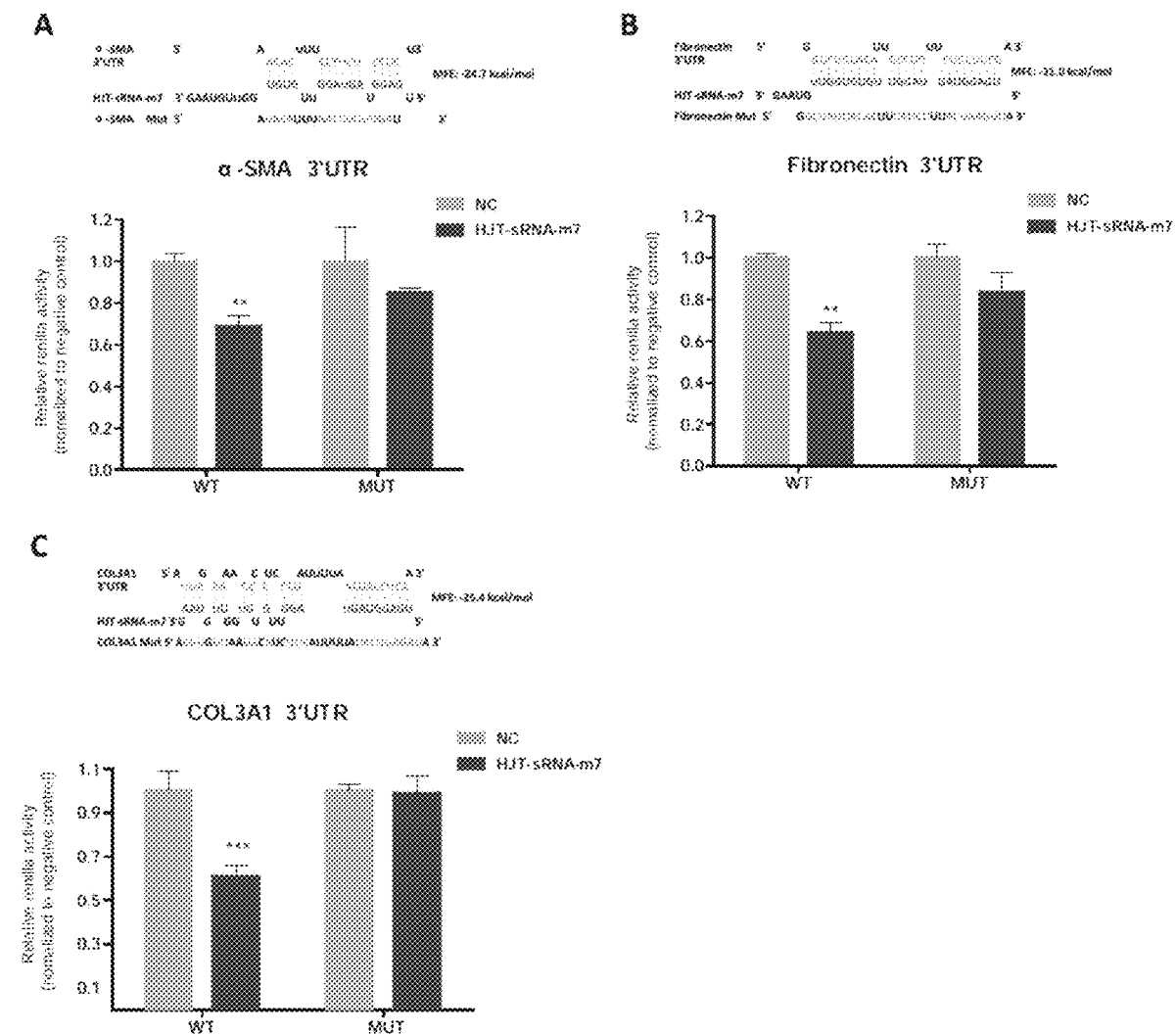
FIGS. 10 to 12 show the results of the luciferase reporter gene assay. Specifically.
Figure 11:
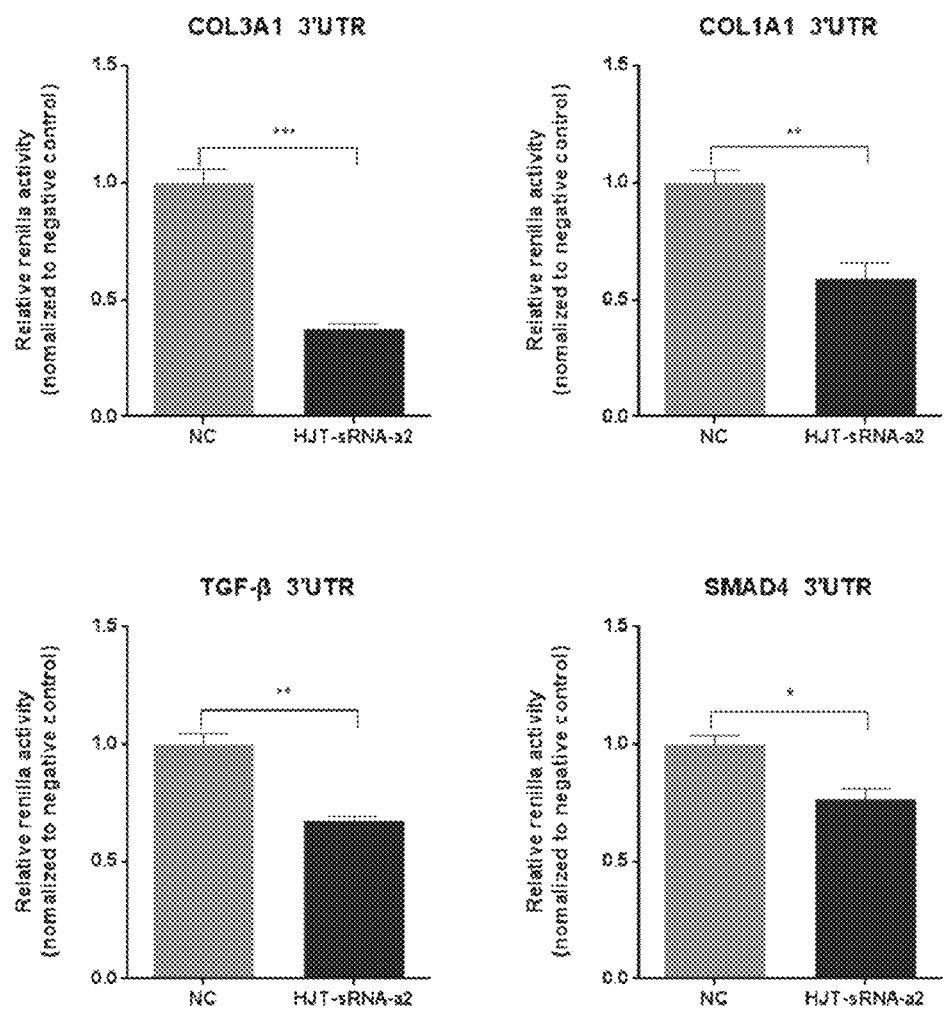
Figure 12:
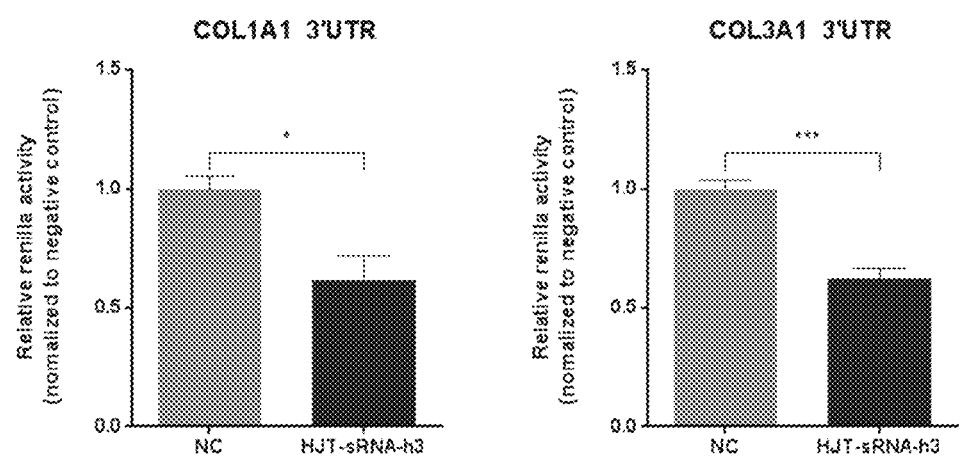

2.2.3 Luciferase Reporter Gene Assay for Detection of Anti-fibrotic Targets of *Rhodiola Rosea*-Derived sRNA Referring to item 1.7 above, the luciferase reporter gene assay system was used to detect intracellular target genes of *Rhodiola rosea*-derived sRNA. As shown in FIGS. 10-12, HJT-sRNA-m7 could exert anti-fibrotic function by directly targeting α-SMA, fibronectin and COL3A1; HJT-sRNA-a2 could exert anti-fibrotic function by directly targeting COL1A1, COL3A1, TGF -β and SMAD; HJT-sRNA-h3 could exert anti-fibrotic function by directly targeting COL1A1 and COL3A1.

The invention claimed is:

1. A method of preventing and/or treating a fibrotic disease and/or syndrome comprising administering to a subject in need thereof a polynucleotide, wherein the polynucleotide comprises a sequence set forth in SEQ ID NO: 8, or a complementary sequence thereof.

2. The method according to claim 1, wherein the fibrotic disease and/or syndrome is a fibrotic disease and/or syndrome of the lung.

3. The method according to claim 1, wherein the fibrotic disease and/or syndrome is selected from the group consisting of
   silicosis, asbestosis, anthracosis, farmer's lung, air-conditioner lung, pigeon-breeder's lung, bagassosis, and familial pulmonary fibrosis.

4. The method according to claim 1, further comprising administering an additional anti-fibrotic agent separately and/or together, temporally and/or spatially, to the subject in need thereof.

5. The method according to claim 4, wherein the additional anti-fibrotic agent is one or more selected from the group consisting of: a glucocorticoid, beclomethasone; an immunosuppressive agent; an antioxidant; an anticoagulant; and colchicine, interferon, ACEI and a statin.

6. The method according to claim 1, wherein the polynucleotide is a small RNA.

7. The method according to claim 1, wherein the polynucleotide is synthetic or expressed from an artificial vector.

8. The method according to claim 5, wherein the glucocorticoid is cortisone acetate, hydrocortisone, prednisolone, dexamethasone, betamethasone, triamcinolone, triamcinolone acetonide, or beclomethasone.

9. The method according to claim 5, wherein the immunosuppressive agent is cyclophosphamide, azathioprine, or methotrexate.

10. The method according to claim 5, wherein the antioxidant is acetylcysteine, carbocisteine.

11. The method according to claim 5, wherein the anticoagulant is low molecular weight heparin.

* * * * *

SEQUENCE LISTING

```
<160> NUMBER OF SEQ ID NOS: 23

<210> SEQ ID NO 1
<211> LENGTH: 22
<212> TYPE: RNA
<213> ORGANISM: Rhodiola Rosea

<400> SEQUENCE: 1
auccccacug cuaaauuuga cu                                              22

<210> SEQ ID NO 2
<211> LENGTH: 25
<212> TYPE: RNA
<213> ORGANISM: Rhodiola Rosea

<400> SEQUENCE: 2
gcuggcccga ugguaguggg uuauc                                           25

<210> SEQ ID NO 3
<211> LENGTH: 27
<212> TYPE: RNA
<213> ORGANISM: Rhodiola Rosea

<400> SEQUENCE: 3 ugggcuacg ccugucugag cgucgcu                                          27

<210> SEQ ID NO 4
<211> LENGTH: 26
<212> TYPE: RNA
<213> ORGANISM: Rhodiola Rosea

<400> SEQUENCE: 4
ugucucguac cgugaguaau aaugcg                                          26

<210> SEQ ID NO 5
<211> LENGTH: 23
<212> TYPE: RNA
<213> ORGANISM: Rhodiola Rosea
```

<400> SEQUENCE: 5
gcugagauga agcacuguag cuc                                             23

<210> SEQ ID NO 6
<211> LENGTH: 26
<212> TYPE: RNA
<213> ORGANISM: Rhodiola Rosea

<400> SEQUENCE: 6
guuauucaag uaauccagga uaggcu                                          26

<210> SEQ ID NO 7
<211> LENGTH: 26
<212> TYPE: RNA
<213> ORGANISM: Rhodiola Rosea

<400> SEQUENCE: 7
ucugagguag uagguuguau gguuau                                          26

<210> SEQ ID NO 8
<211> LENGTH: 27
<212> TYPE: RNA
<213> ORGANISM: Rhodiola Rosea

<400> SEQUENCE: 8
guauguaaac auccucgacu ggaagcu                                         27

<210> SEQ ID NO 9
<211> LENGTH: 25
<212> TYPE: RNA
<213> ORGANISM: Rhodiola Rosea

<400> SEQUENCE: 9
guuaugaggu aguagauugu auagu                                           25

<210> SEQ ID NO 10
<211> LENGTH: 28
<212> TYPE: RNA
<213> ORGANISM: Rhodiola Rosea

<400> SEQUENCE: 10
ugagguagua gguugugugg uuguaagc                                        28

<210> SEQ ID NO 11
<211> LENGTH: 28
<212> TYPE: RNA
<213> ORGANISM: Rhodiola Rosea

<400> SEQUENCE: 11
gacggucgua ccgugaguaa uaaugcga                                        28

<210> SEQ ID NO 12
<211> LENGTH: 19
<212> TYPE: RNA
<213> ORGANISM: Rhodiola Rosea

<400> SEQUENCE: 12
uagcaccauu gaaaucagu                                                  19

<210> SEQ ID NO 13
<211> LENGTH: 21
<212> TYPE: RNA
<213> ORGANISM: Rhodiola Rosea

<400> SEQUENCE: 13
uagcaccauc cgaaaucggu a                                              21

<210> SEQ ID NO 14
<211> LENGTH: 23
<212> TYPE: RNA
<213> ORGANISM: Rhodiola Rosea

<400> SEQUENCE: 14 ugggacucg aagacgauca uau                                             23

<210> SEQ ID NO 15
<211> LENGTH: 21
<212> TYPE: RNA
<213> ORGANISM: Rhodiola Rosea

<400> SEQUENCE: 15
uuuggauuga agggagcucu g                                              21

<210> SEQ ID NO 16
<211> LENGTH: 21
<212> TYPE: RNA
<213> ORGANISM: Rhodiola Rosea

<400> SEQUENCE: 16
cagccaagga ugacuugccg g                                              21

<210> SEQ ID NO 17
<211> LENGTH: 21
<212> TYPE: RNA
<213> ORGANISM: Rhodiola Rosea

<400> SEQUENCE: 17
uccacaggcu uucuugaacu g                                              21

<210> SEQ ID NO 18
<211> LENGTH: 53
<212> TYPE: DNA
<213> ORGANISM: Artificial Sequence
<220> FEATURE:
<223> OTHER INFORMATION: Synthetic primer

<400> SEQUENCE: 18
gtcgtatcca gtgcagggtc cgaggtattc gcactggata cgacaaaaat atg          53

<210> SEQ ID NO 19
<211> LENGTH: 52
<212> TYPE: DNA
<213> ORGANISM: Artificial Sequence
<220> FEATURE:
<223> OTHER INFORMATION: Synethetic primer

<400> SEQUENCE: 19
gtcgtatcca gtgcacgctc cgaggtattc gcactggata cgacgcttac aa           52

<210> SEQ ID NO 20
<211> LENGTH: 18
<212> TYPE: DNA
<213> ORGANISM: Artificial Sequence
<220> FEATURE:
<223> OTHER INFORMATION: Synthetic primer

<400> SEQUENCE: 20

```
gcgcgtcgtg aagcgttc                                                       18

<210> SEQ ID NO 21
<211> LENGTH: 16
<212> TYPE: DNA
<213> ORGANISM: Artificial Sequence
<220> FEATURE:
<223> OTHER INFORMATION: Synthetic primer

<400> SEQUENCE: 21
gtgcagggtc cgaggt                                                         16

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
tcgcgctgag gtagtaggtt                                                     20

<210> SEQ ID NO 23
<211> LENGTH: 16
<212> TYPE: DNA
<213> ORGANISM: Artificial Sequence
<220> FEATURE:
<223> OTHER INFORMATION: Synthetic primer

<400> SEQUENCE: 23
gtgcacgctc cgaggt                                                         16
```